United States Patent [19]

Hassler et al.

[11] Patent Number: 4,979,500
[45] Date of Patent: Dec. 25, 1990

[54] EXTRACORPOREAL LITHOTRIPSY APPARATUS WITH TRANSVERSELY ADJUSTABLE FOCUS REGION

[75] Inventors: Dietrich Hassler, Uttenreuth; Erhard Schmidt, Erlangen; Helmut Reichenberger, Eckental, all of Fed. Rep. of Germany

[73] Assignee: Siemens Aktiengesellschaft, Berlin and Munich, Fed. Rep. of Germany

[21] Appl. No.: 388,859

[22] Filed: Aug. 3, 1989

[30] Foreign Application Priority Data

Aug. 17, 1988 [EP] European Pat. Off. ........ 88113361.5

[51] Int. Cl.$^5$ .............................................. A61B 17/22
[52] U.S. Cl. .............................. 128/24 A; 128/660.03
[58] Field of Search .................... 128/24 A, 660.03; 606/127, 128, 24 EL

[56] References Cited

U.S. PATENT DOCUMENTS

| | | |
|---|---|---|
| 3,913,061 | 10/1975 | Green . |
| 4,131,021 | 12/1978 | Mezrich et al. . |
| 4,620,545 | 11/1986 | Shene et al. ............... 128/24 A |
| 4,664,111 | 5/1987 | Reichenberger ............ 128/24 A |
| 4,834,106 | 5/1989 | Hassler et al. ............. 128/24 A |
| 4,928,672 | 5/1990 | Reichenberger ............ 128/24 EL |

FOREIGN PATENT DOCUMENTS 3703336 8/1988 Fed. Rep. of Germany ...... 128/328

Primary Examiner—Lee S. Cohen
Assistant Examiner—John D. Zele
Attorney, Agent, or Firm—Hill, Van Santen, Steadman & Simpson

[57] ABSTRACT

An extracorporeal lithotripsy apparatus includes a shock waves source which generates shock wave along an acoustic axis in a propagation direction, with the shock waves being caused to converge, either by a curvature of the shock wave source or by the use of a separate focusing element, at a focus region, the lithotripsy apparatus being initially positioned so that a calculus to be disintegrated is coincident with the focus region. During treatment, the calculus may be displaced from its original, identified position by patient movement, such as due to respiration. In addition to permitting adjustment of the position of the focus region along the longitudinal axis of the shock wave source, adjustable shock wave deflection elements are provided which are pentrated by the shock waves and which interact with the shock waves to deflect the shock waves and thereby cause the acoustic axis to deviate from the longitudinal axis, for permitting selected lateral adjustment of the positon of the focus region to accommodate lateral displacement of the calculus and maintain coincidence of the focus region and the calculus.

16 Claims, 2 Drawing Sheets

EXTRACORPOREAL LITHOTRIPSY APPARATUS WITH TRANSVERSELY ADJUSTABLE FOCUS REGION

BACKGROUND OF THE INVENTION

1. Field of the Invention

The present invention is directed to an extracorporeal lithotripsy apparatus, and in particular to such an apparatus including means for laterally adjusting the position of the focus region so that a calculus which has been laterally displaced from an initial position can still be maintained within the focus region for effective disintegration.

2. Description of the Prior Art

Extracorporeal lithotripsy devices are known in the art which include a shock wave source for generating a shock wave in a shock wave transmitting medium, with the shock wave being focused at a focus region. The apparatus is initially positioned so that the focus region is coincident with a calculus to be disintegrated in the body of a patient. Devices of this type are used in medicine, for example, to disintegrate gallstones and kidney stones. The use of these devices is advantageous because a surgical operation or the use of invasive probes are not required, and therefore injury to the patient and the risk of infection are minimized.

An example of such an extracorporeal lithotripsy apparatus is described in German OS No. 33 280 39. The shock waves generated by a shock wave source are coupled into the body of a patient via medium which transmits the shock waves. In the body of the patient, the shock waves are focused, for example, onto a kidney stone and transfer a portion of their energy in the form of compressive and tensile forces, resulting in disintegration of the calculus. Focusing of the shock wave may be done, for example, with an acoustic lens. The focus region in the body of the patient can be displaced along the acoustic axis of the shock waves by displacing the acoustic lens along that same direction. The focus region can thus follow a change in the location of the calculus along the acoustic axes.

Due to respiration or other movement, however, the calculus may also change position transversely relative to the acoustic axis. In the conventional devices, the only way to adjust the position of the focal region to follow a transverse movement of the calculus is to transversely adjust the acoustic axis of the shock wave source. This requires that the shock wave source, or the housing containing the shock wave source, be mounted to permit universal pivoting of the shock source, together with the acoustic lens.

Due to the masses which must be moved, such lateral adjustment is very sluggish, so that the focus region can only be adjusted to accommodate relatively slow changes in the position of the calculus. Changes in the location of the calculus which are caused by respiration are relatively rapid, and a follow-up adjustment of the focus region, if possible at all, can only be accomplished with difficulty in a conventional device. If such a follow-up adjustment is not undertaken, the shock wave source can only be activated when the calculus is again situated in the focus region, thereby significantly lengthening the treatment time.

An ultrasound diagnostic apparatus is described in U.S. Pat. No. 3,913,061 wherein the ultrasound echoes, reflected by an examination subject, are focused onto a linear array and can be deflected along the linear array. The apparatus also includes two acoustic lenses by which the reflected ultrasound signals are focused on to the linear array. This ultrasound apparatus also includes two elements each having a wedge-shaped longitudinal section, which are mounted to be rotatable around a common axis in the region between the acoustic lenses. These elements are aligned transversely relative to the propagation direction of the ultrasound signals. The wedge-shaped elements are offset by 180° relative to each other and are rotatable around the common axis with a drive mechanism in different rotational directions, but with the same angular speed. Upon rotation of the elements surround the common axis, the ultrasound signals reflected by the examination subject, and focused onto the linear array by the acoustic lens, are deflected along the linear array in oscillating fashion. The acoustic lenses and the wedge-shaped elements are disposed in a medium which transmits the ultrasound signals.

SUMMARY OF THE INVENTION

It is the object to the present invention to provide an extracorporeal lithotripsy apparatus which permits deflection of the acoustic access of the shock waves perpendicularly (transverse) to the shock wave propagation direction in a manner which does not require the inertia of the shock wave source or the housing containing the shock waves source to be overcome.

The above object is achieved in accordance with the principles of the present invention in an extracorporeal lithotripsy apparatus having an acoustic deflection stage, which includes one or more acoustic deflection elements, each in the form of a disk having a wedge-shaped longitudinal section, which are adjustable in a plane substantially perpendicular to the propagation direction of the shock waves, with the adjustment of the deflection element causing a displacement of the acoustic axis of the shock wave perpendicularly to the propagation direction.

Due to the relatively low mass of the deflection element, the acoustic access of the shock wave can follow a rapid change in position of the calculus, such as a respiration-induced change, in a substantially inertia-free manner. This permits the shock wave source to be more frequently activated, since the calculus will more often reside within the focus zone, so that the treatment time can be shorted.

A further advantage is that the housing containing the shock wave source can be arranged at a location on the surface of the body of the patient at which an optimally good shock wave application is possible. In conventional lithotripsy devices, the housing for the shock wave generator had to be positioned on the surface of the body at a location such that the straight line acoustic axis of the shock wave source passed through the calculus to be disintegrated. By having the capability of laterally displacing the focus region lithotripsy apparatus constructed in accordance with the principles of the present invention, the housing for the shock wave source can be positioned on the surface of the body of the patient at a location where the acoustic axis, if it coincided with the central longitudinal access of the housing, would miss the calculus, and the acoustic axis can then be laterally displaced by adjusting the deflection element or elements.

If the shock wave source is planar, and a separate focusing element is provided, the deflection element may be disposed between the shock wave source and the focusing element. Alternatively, the shock wave source may be curved, so that focusing of the shock wave is effected by the shock wave source itself. A further alternative in accordance with the principles of the present invention is to use two deflection elements which in combination form a means for focusing the shock waves as well as means for deflecting the shock waves.

DESCRIPTION OF THE PREFERRED EMBODIMENTS

Figure 1:
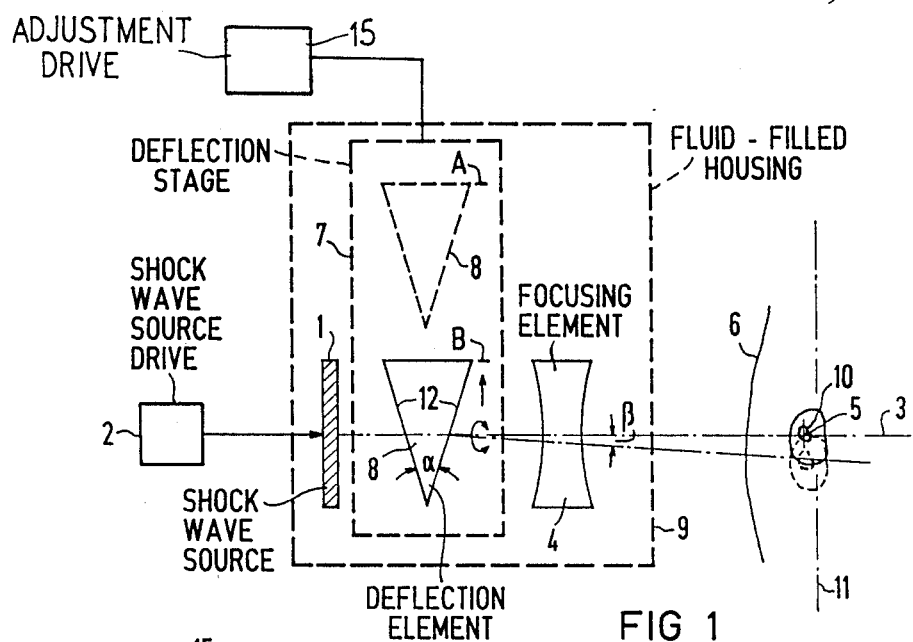
FIG. 1 is a schematic diagram showing the basic components of an extracorporeal lithotripsy apparatus constructed in accordance with the principles of the present invention.

As shown in FIG. 1, an extracorporeal lithotripsy apparatus constructed in accordance with the principles of the present invention includes a shock wave source 1 which is operated by a drive circuit 2 for generating shock waves in a known manner. The shock waves source 1 and the shock waves drive circuit 2 may be as disclosed, for example, in German OS No. 3328039. The shock waves source 1 has an acoustic axis 3 along which emitted shock waves propagate in a direction toward a focusing element 4, which may be an acoustic lens. The focusing element 4 focuses the shock waves so that they converge in a focus region 10, which substantially coincides with a calculus 5 which is to be disintegrated in the body 6 of a patient.

In accordance with the principles of the present invention, the lithotripsy apparatus of FIG. 1 also includes an acoustic deflection stage 7 disposed between the shock waves source 1 and the focusing element 4. It is also possible to arrange the deflection stage 7 following the focusing element 4 in the direction of shock wave propagation. The deflection stage 7 includes a deflection element 8, which is a disc having a wedge-shaped longitudinal direction. The deflection element 8 is adjustable in position in a plane substantially perpendicular to the acoustic axis 3.

The shock wave source 1, the focusing element 4, the deflection stage 7, as well as other common components of the lithotripsy apparatus, which have been omitted for clarity because they are not required to explain the invention, are contained within a fluid-filled housing 9, the fluid in the housing 9 being a good shock wave transmissive medium. The housing 9 may, for example, be a bath in which the patient is also situated, or may be a shock way tube which includes a bellows (not shown) for coupling the shock waves into the patient in a known manner. The side of the bellows in direct contact with the surface of the body 6 of the patient may be coated with an application gel.

As described, for example, in the aforementioned German No. OS3328039, the shock wave source 1, or the body 6 of the patient, or both, is position so that the focus region 10 coincides with the position of the calculus 5. For this positioning the deflection element 8 is not needed, and may be located in a standby position A indicated with dashed lines in FIG. 1. During treatment, the position of the calculus 5 may change in a direction substantially perpendicular to the acoustic axis 3, such as due to respiration or due to the action of the shock waves on the calculus. Lateral adjustment of the acoustic axis 3, permitting a follow-up adjustment of the position of the focal region 10, is undertaken by positioning the deflection element 8 in the path of the shock waves as indicated at B in FIG. 1, by means of a schematically shown adjustment drive 15, thereby permitting follow-up adjustment of the position of the focus region 10. In FIG. 1 the calculus 5 is shown to have been dislocated in the direction of the longitudinal axis 11 of the patient.

Figure 3:
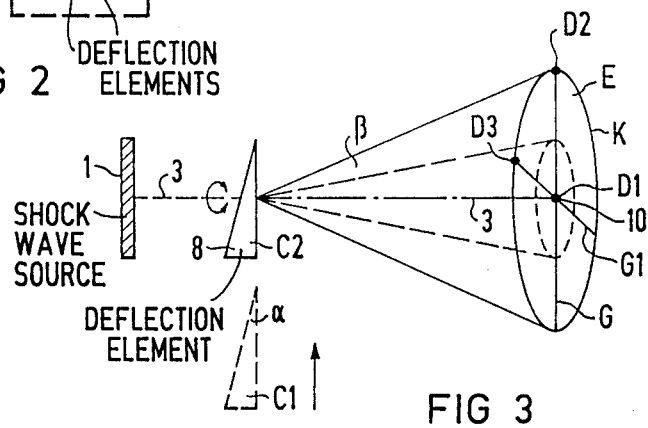
FIG. 3 is a schematic diagram for explaining the operation of all embodiments of an extracorporeal lithotripsy apparatus constructed in accordance with the principles of the present invention.

The shock waves are deflected and the acoustic axis 3 is thereby translated by an angle $\beta$ which is dependent on the speed of sound within the deflection element 8, the speed of sound in the medium surrounding the deflection element 8, and on the angle $\alpha$ subtended by the lateral surfaces 12 of the deflection element 8. An explanatory example is shown in FIG. 3, which shows a plane E within which the focus region 10 can be deflected. Only the relative positions of the shock wave source 1, the deflection element 8 and the focus region 10 are necessary to explain the operation, therefore other elements have been omitted for clarity in FIG. 3. If the deflection element is in the position C1 indicated by dashed lines, no translation of the acoustic axis 3 occurs, and thus no change in the position of the focus region 10 occurs. It is assumed that the focus region 10 in the plane E is initially at position D1. The deflection element 8 is then moved to position C2, causing the acoustic axis 3 to be deflected by an angle $\beta$. As described above, the amount of deflection, i.e., the magnitude of the angle $\beta$ is dependent upon the angle $\alpha$ of the deflection element 8, and the speed of sound in the deflection element 8 and in the surrounding medium. This causes the focus region 10 to move to position D2 in the plane E. Rotation of the deflection element 8, while in the position C2 around the acoustic axis 3 by a selective angular amount causes the focus region 10, for example, to be displaced from the position D2 in the plane E to the position referenced D3 in the plane E. A continuous rotation of the deflection element 8 around the acoustic axis 3 causes the focus region 10 to rotate along a circular orbit referenced K in the plane E.

By adding a further deflection element 8 (not shown in FIG. 3) or by modifying the angular $\alpha$ of the deflection element 8, the magnitude of the angle $\beta$ by which the acoustic axis 3 is deflected can be varied.

Only one embodiment of the deflection element 8 is shown in FIG. 1, wherein the both of the surfaces 12 are disposed at an angle other than 90° relative to the acoustic axis 3. It is also possible, however, to have one surface 12 of the deflection element 8 disposed of perpendicularly relative to the acoustic axis 3. In another embodiment, one surface 12 may have a varying slope.

Figure 2:
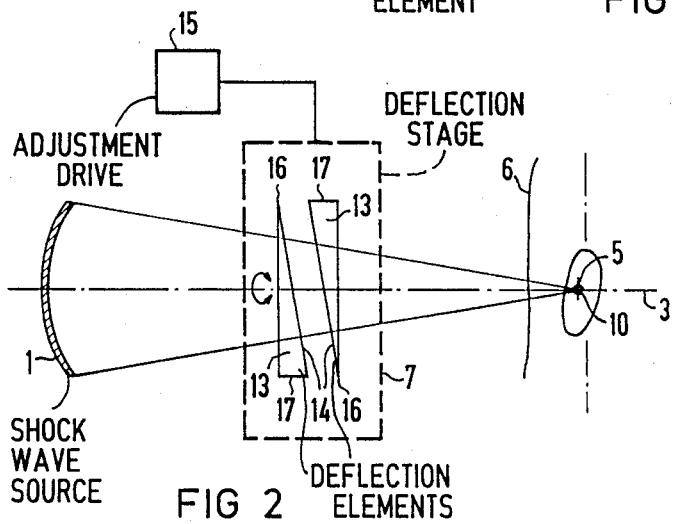
FIG. 2 is a schematic diagram showing the basic components of a further embodiment of an extracorporeal lithotripsy apparatus constructed in accordance with the principles of the present invention.

A further exemplary embodiment of a lithotripsy apparatus constructed in accordance with the principles of the present invention is shown in FIG. 2. Again, components is not necessary for a description of the invention are omitted. In this embodiment, the shock wave source 1 is curved, so that a separate focusing element is not needed. In this embodiment, the deflection stage 7 includes two deflection elements 13, each in the shape of a circular disc having a wedge-shaped longitudinal section. Both elements 13 are mounted to be rotatable around a central longitudinal axis. The central longitudinal axis coincides with the acoustic axis. The surfaces 14 of the elements 13 proceed at an angle relative to the acoustic axis 3 and face each other. It is also possible to adjust the surfaces 14 in a direction toward the shock wave source 1 or in a direction toward a body 6, or to adjust the surface 14 of one element 13 in the direction of the shock waves source 1 and the surface 14 of the other deflection element 13 in the direction of the body 6. Such adjustment can be accomplished by movement by one or both of the elements 13 along the acoustic axis 3, by tilting one or both of the elements 13, or by a combination of movement and tilting.

Rotation of the deflection elements 13 around the central longitudinal axis is undertaken by an adjustment drive 15 which may be as described, for example, in U.S. Pat. No. 3,913,061. The adjustment drive 15 may rotate the deflection elements 13 in the same rotational direction or in opposite rotational directions, and may rotate the deflection elements 13 with the same angular speed or with different angular speeds. It is also possible to rotate 1 deflection element 13 while retaining the other deflection element 13 stationary.

Rotation of the elements 13 in the same rotational direction causes the focus region 10 to rotate on the circular orbit K described in FIG. 3. The greatest amount of displacement of the focus region 10, i.e., the longest circular orbit K, is achieved when the respective wedge tips 16 of the displacement elements 13 are in registry (i.e., when one tip exactly overlaps the other, as "seen" by the incoming shock wave), or when the respective wedge ends 17 of the displacement elements 13 are in registry, with the registry being maintained during rotation around the central longitudinal access. No displacement of the focus region 10 is achieved at all if the wedge tip 16 of a displacement element 13 and a wedge end of the other displacement element 13 are in registry, and the displacement elements 13 are identically fashioned. Every other relationship of the wedge tips 16 or the wedge ends 17 relative to each other causes a change in the diameter of the circular orbit K. If the deflection elements 13 are rotated in opposite directions with the same angular speed around the central longitudinal axis, the focus region 10 will be displaced along a straight line G in the plane E perpendicular to the acoustic axis 3, as also shown in FIG. 3. Adjustment of the deflection elements 13 relative to each other causes the straight line G to be rotated in the plane E. As shown in FIG. 3, the focus region 10 is then deflected, for example, along a straight line G1 in the plane E.

Rotating the deflection elements 13 at respectively different angular speeds causes the focus region 10 to be deflected in the plane E along paths which deviate from a straight line.

The curved shock wave source 1 shown in FIG. 2 may be replaced by a planar shock wave source. If a planar shock wave source is used, the deflection elements may be structured to simultaneously function as a focusing element so that the surface of the deflection element 13 which is first in the direction of shock wave propagation (i.e., the surface which faces the shock waves source 1) may be concave, and the surface of the other deflection element 13 which is last in the direction of shock wave propagation (i.e., the surface which faces the body 6) may also be concave. The combined effect of these two concave surfaces is to focus the shock waves unto the calculus 5 and an additional focusing element, such as the aforementioned acoustic lens, can be omitted. The embodiments shown in FIGS. 1 and 2 are only exemplary embodiments for the acoustic deflection stage 7. Other embodiments may be apparent which make use of at least one deflection element which is adjustable in a plane approximately perpendicular to the acoustic axis of the shock wave source, to cause a lateral deflection of the acoustic axis.

Such a further embodiment is shown in FIG. 3, which includes a system for locating and displaying the calculus to be disintegrated. The locating and display system may, for example, be a conventional ultrasound system, including an ultrasound transmitter/receiver 18, and ultrasound processor 19, and a display 20 on which the examination region is portrayed. The ultrasound transmitter/receiver is guided through central openings in the shock wave source 1 and the deflection elements 13, so as to be adjustable in a direction along the acoustic axis 3, and rotatable around the acoustic axis 3. In the exemplary embodiment in FIG. 4, the ultrasound system is a B-scan system, permitting display of a plane of an examination region on the display 20.

Figure 4:
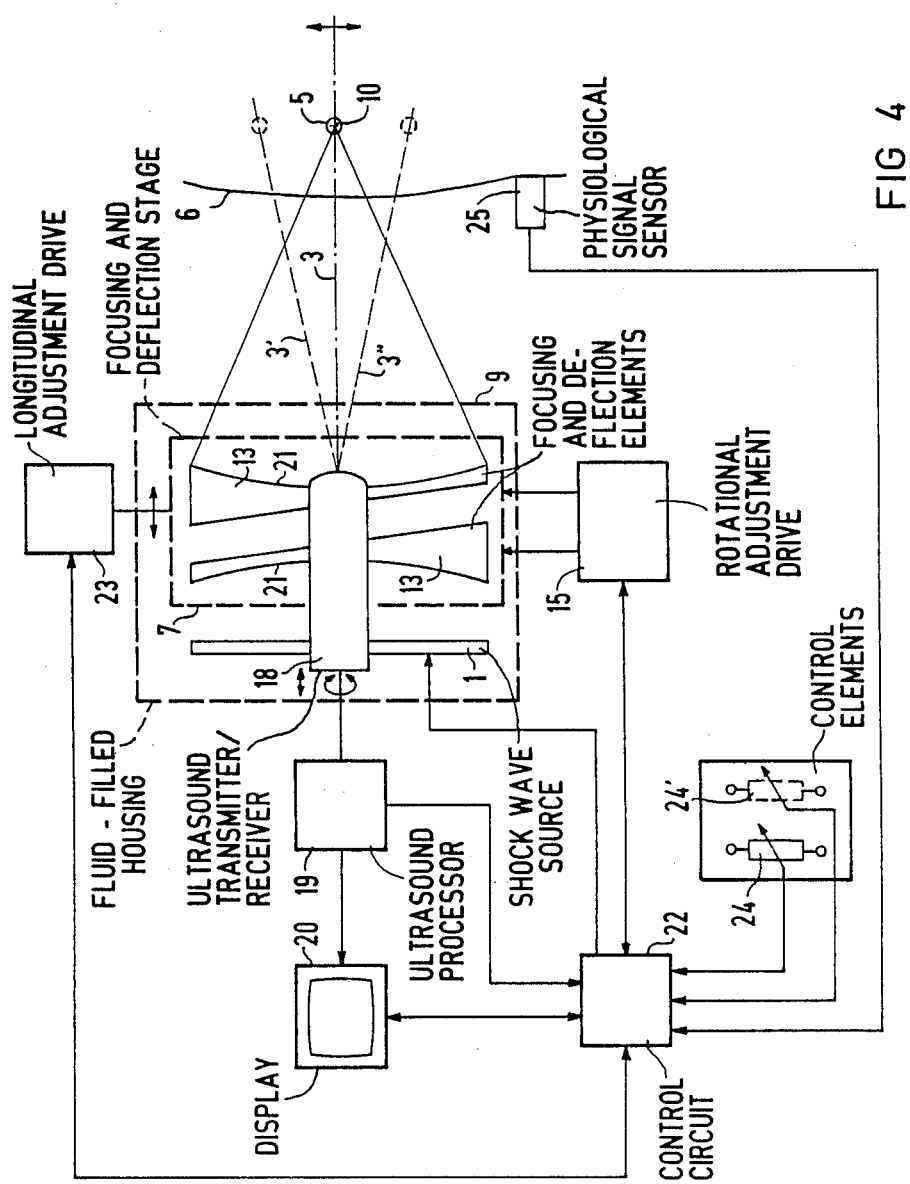
FIG. 4 is a schematic diagram showing the basic components of another embodiment of an extracorporeal lithotripsy apparatus constructed in accordance with the principles of the present invention.

The deflection elements 13 in the embodiment of FIG. 4 have respective outer surfaces which are concave, as described above, so that a separate focusing element is not needed.

Locating a display of the calculus 5 can be undertaken as described in German No. OS3328039. A mark or an outline identifying the focus region can be mixed into the image on the screen of the display 20. The mark and the calculus 5, which is also visible on the screen, are brought into coincidence by adjusting the position of the body 6 relative to the housing 9, or by changing the location of the housing 9 relative to the body 6, or by adjusting the deflection stage 7 in the direction of the acoustic axis 3. The focus region of the shock wave in the body 6 is then situated in the region of the calculus 5. If the calculus 5 is dislocated in a plane perpendicular to the acoustic axis 3, such as due to respiration, this dislocation will be visible on the screen on the display 20. Adjustment of the focus region 10 in the direction of the changed position of the calculus 5 can be achieved by operating the adjustment drive 15 via a control circuit 22, so that the mark on the display 20 indicating the focus region, as well as the actual focus region 10, oscillates in a manner corresponding to the change in the position of the calculus 5. To accomplish this, the adjustment drive 15 causes the deflection elements 13 to be rotated around the central longitudinal axis in different rotational directions but with the same angular speed.

The extreme positions of the acoustic axis 3 are indicated with dashed lines 3' and 3". The shock wave source 1 is activated by the control circuit 22 when a further, controllable mark, which can be re-adjusted to coincide with a calculus 5, appears on the screen of the display 20 coincident with the mark indicating the focus region of the shock waves. This follow-up adjustment of the controllable mark can be undertaken with a control element 24, for example, a tracking ball (mouse) whose signals are supplied to a mark generator circuit within the control circuit 22. For shortening the treatment time, the frequency of the excursion of the focus region 10 is made higher than the respiratory frequency when, for example, gallstones are to be treated. The focus region 10 and the calculus 5 then coincide more frequently, so that the shock wave source 1 can be more frequently activated.

Marks can also be portrayed on the screen of the display 20 in the region of the change in location of the calculus 5. The shock waves source 1 may be activated when the mark identifying the focus region of the shock waves is situated in the region of these other marks, and a signal is generated which correlates with the change in position of the calculus 5. A signal dependent on respiration may, for example, be used. The focus region 10, however, may alternatively be manually or automatically readjusted to a change in location of the calculus 5 by operating the adjustment drive 15.

For example, a manual follow-up adjustment of the mark identifying the focus region on the screen of the display 20 may be accomplished by the operator following a change in the location of the calculus 5 by, means of the manually actuateable control element 24. The control signal from the control element 24 is supplied via the control circuit 22 to the acoustic deflection stage 7. The deflection element 13 are adjusted relative to each other so that the focus region 10 of the shock wave in the body 6 follows the change in the location of the calculus 5. A continuous rotation of the elements 13 is not needed for this purpose. Via a further control element 24', a longitudinal adjustment drive 23, which causes the acoustic deflection stage 7 to be moved along the acoustic axis 3, can be operated via the control circuit 22 to position the focus region 10 at a proper depth within the body 6.

At least two B-scan planes are preferably displayed on the screen on the display 20 for portraying the calculus 5. Topical changes of the calculus 5 are visible by means of these images. For that purpose, the ultrasound transmitter/receiver 18 can be rotated by a defined angular amount the acoustic axis 3. It is also possible to use a further ultrasound unit (not shown), so that the B-scan planes can have different spacial orientations. A mark indicating the focus region of the shock wave is visible in each image of the B-scan plane. For disintegrating the calculus 5, these marks are brought into coincidence with the calculus 5 on the screen of the display 20 by adjusting the control elements 24 and/or 24' so that the shock wave source 1 can then be activated. It is also possible to portray three or more B-scan planes on the screen of the display 20, so that the change in position of the calculus 5 within a volume can be portrayed.

For example, three B-scan planes which are parallel to each other can be shown on the display 20. The calculus 5 should then be portrayed in the middle B-scan plane on the display 20. If the calculus 5 appears on either of the other B-scan images, this indicates a change in position of the calculus 5, and follow-up adjustment of the position of the focus region 10 can be undertaken by adjusting the deflection stage 7 or adjusting the position of the housing 9. It is preferable to again portray the calculus 5 in the middle B-scan plane after such re-adjustment.

An automatical adjustment of the focus region 10 of the shock wave can be undertaken, for example, by mixing marks indicating a maximum position change of the calculus 5 in each of the B-scan planes into the images on the display 20. A computer within the control circuit 22 can then, based on coordinates corresponding to those marks, calculate the expected position of the calculus 5 between those maxima at any given time. Alternatively, a physiological signal sensor 25, such as a respiration sensor, maybe applied to the body 6 of the patient, and the calculation in the computer within the control circuit 22 can be made based on signals from this sensor 25. The focus region 10 can then be automatically readjusted via the control circuit 22 by operating the adjustment drives 15 and 23.

The control circuit 22 may alternatively be capable of automatic image evaluation, so that the coordinate corresponding to any change in position of the calculus 5 can be determine, and focus region 10 can be automatically re-adjusted based on these coordinates.

It is also possible to use an X-ray system as the locating system instead of an ultrasound system.

Although other modifications and changes may be suggested by those skilled in the art, it is the intentions of the inventors to embody within the patent warranted hereon all changes and modifications as reasonably and properly comes in the scope of their contribution to the art.

We claim as our invention:

1. An extracorporeal lithotripsy apparatus for treating a calculus in a patient, said apparatus comprising;
    means for generating shock waves propagating along an acoustic axis, said means for generating shock waves having a longitudinal axis;
    means for focusing said shock waves along said longitudinal axis to a focus region;
    means for coupling said shock waves into a patient, said means for coupling including a shock wave-transmitting medium and a container housing said medium in which said means for generating shock waves and said means for focusing are disposed; and
    means disposed in said medium in a propagation path of said shock waves which is penetrated by and interacts with said shock waves for deflecting said shock waves so that said acoustic axis deviates from said longitudinal axis to change the position of said focus region in a plane substantially perpendicular to said longitudinal axis to bring said focus region and a calculus in said patient into coincidence, said means for deflecting including a disc having a wedge-shaped longitudinal section, and means for adjusting the position of said disc in a further plane substantially perpendicular to said longitudinal axis.

2. An apparatus as claimed in claim 1 wherein said means for deflecting includes a further disc having a wedge-shaped longitudinal section, said means for deflecting having a central longitudinal axis extending through each of said disc and said further disc, and wherein said means for adjusting is a means for rotating each of said disc and said further disc around said central longitudinal axis of said means for deflecting.

3. An apparatus as claimed in claim 2 wherein said disc and said further disc are identically shaped.

4. An apparatus as claimed in claim 2 wherein said means for adjusting is a means for individually rotating each of said disc and said further disc around said central longitudinal axis of said means for deflecting.

5. An apparatus as claimed in claim 4 wherein said means for adjusting is a means for rotating said disc and said further disc around said central longitudinal axis of said means for deflecting in different rotational directions.

6. An apparatus as claimed in claim 4 wherein said means for adjusting is a means for rotating each of said disc and said further disc around said central longitudinal axis of said means for deflecting with the same angular speed.

7. An apparatus as claimed in claim 4 wherein said means for adjusting is a means for rotating each of said disc and said further disc around said central longitudinal axis of said means for deflecting with selected respectively different angular speeds.

8. An apparatus as claimed in claim 1 further comprising:
   means for locating and displaying a visual image of a region in said patient in which said calculus is disposed and from which a change in position of said calculus can be seen; and
   means for controlling said means for adjusting the position of said disc to change the position of said focus region in said plane, based on said image, so that said focus region follows said change in position of said calculus.

9. An apparatus as claimed in claim 8 wherein said means for controlling is means for automatically operating said means for adjusting the position of said disc to substantially maintain said calculus in coincidence with said focus region.

10. An apparatus as claimed in claim 8 further comprising means for activating said means for generating said shock waves when said calculus is disposed within said focus region.

11. An apparatus as claimed in claim 8 wherein said means for locating and displaying includes means for generating a mark within said visual image, said mark identifying the position of said focus region, and wherein said means for controlling includes means for changing the position of said mark within said visual image with a corresponding adjustment of said disc by said means for adjusting.

12. An apparatus as claimed in claim 11 further comprising means for activating said shock wave source when the image of said calculus on said display is within said mark identifying said focus region.

13. An apparatus as claimed in claim 1 wherein said means for focusing is a separate focusing element disposed following said means for deflecting in the direction of propagation of said shock waves.

14. An apparatus as claimed in claim 1 wherein said means for focusing is a curved surface of said means for generating shock waves.

15. An extracorporeal lithotripsy apparatus for treating a calculus in a patient, said apparatus comprising:
   means for generating shock waves propagating along an acoustic axis, said means for generating shock waves having a longitudinal axis;
   means for focusing said shock waves along said longitudinal axis to a focus region;
   means for coupling said shock waves into a patient, said means for coupling including a shock wave-transmitting medium and a container housing said medium in which said means for generating shock waves and said means for focusing are disposed; and
   a deflection element disposed in said medium and penetrated by said shock waves, said deflection element consisting of material which interacts with said shock waves and having shape, said shape and material being selected in combination for deflecting said shock waves so that said acoustic axis deviates from said longitudinal axis to change the position of said focus region in a plane substantially perpendicular to said longitudinal axis so that said focus region coincides with a calculus in said patient.

16. An extracorporeal lithotripsy apparatus for treating a calculus in a patient, said apparatus comprising:
   means for generating shock waves propagating along an acoustic axis, said means for generating shock waves having a longitudinal axis;
   means for coupling said shock waves into a patient, said means for coupling including a shock wave-transmitting medium and a container housing said medium in which said means for generating shock waves is disposed;
   first and second defection elements disposed in succession in said medium and penetrated by said shock waves, each of said first and second deflection elements having a longitudinal section varying in thickness so that shock waves passing through each deflection element are caused to deviate from said longitudinal axis by an angle dependent upon the location at which said shock wave passes through the deflection element, each of said first and second deflection elements having an outer concave surface which focuses shock waves passing therethrough to a focus region;
   means for adjusting the position of said first and second deflection elements along said longitudinal axis to adjust the position of said focus region along said longitudinal axis; and
   means for adjusting the position of each of said first and second deflection elements in a plane perpendicular to said longitudinal access to adjust the position of said focus region in a further plane perpendicular to said longitudinal axis.

* * * * *